United States Patent

Kato et al.

[11] Patent Number: 5,238,552
[45] Date of Patent: Aug. 24, 1993

[54] OXYGEN SENSOR

[75] Inventors: Nobuhide Kato, Aichi; Yasuhiko Hamada, Nagoya, both of Japan

[73] Assignee: NGK Insulators, Ltd., Nagoya, Japan

[21] Appl. No.: 893,818

[22] Filed: Jun. 4, 1992

[30] Foreign Application Priority Data

Jul. 23, 1991 [JP] Japan .................. 3-182285

[51] Int. Cl.5 ........................................ G01N 27/26
[52] U.S. Cl. ..................................................... 204/428
[58] Field of Search ............................ 204/428, 429

[56] References Cited

U.S. PATENT DOCUMENTS

| | | | |
|---|---|---|---|
| 3,891,529 | 6/1975 | Beesch | 204/428 |
| 4,038,034 | 7/1977 | Nakajima et al. | 23/255 |
| 4,065,372 | 12/1977 | Hacker et al. | 204/428 |
| 4,111,778 | 9/1978 | Davis et al. | 204/428 |
| 4,283,261 | 8/1981 | Maurer et al. | 204/428 |
| 4,401,967 | 8/1983 | Miwa et al. | 338/34 |
| 4,507,192 | 3/1985 | Ebizawa et al. | 204/428 |
| 4,597,850 | 7/1986 | Takahasi et al. | 204/426 |
| 4,624,770 | 11/1986 | Yamada et al. | 204/428 |
| 4,683,049 | 7/1987 | Nakajima et al. | 204/428 |
| 4,689,136 | 8/1987 | Nakajima et al. | 204/428 |

FOREIGN PATENT DOCUMENTS

| | | |
|---|---|---|
| 2304359 | 8/1974 | Fed. Rep. of Germany . |
| 2326086 | 12/1974 | Fed. Rep. of Germany . |
| 2348505 | 4/1975 | Fed. Rep. of Germany . |
| 2855012 | 6/1980 | Fed. Rep. of Germany . |
| 1469698 | 4/1977 | United Kingdom . |

Primary Examiner—John Niebling
Assistant Examiner—Bruce F. Bell
Attorney, Agent, or Firm—Shea & Gould

[57] ABSTRACT

A bottomed, inner cylindrical member 21 is placed around a sensor element 2, and a bottomed, outer cylindrical member 24 is located around this inner cylinder 21. The inner cylinder 21 includes a hole 21a at a location opposite to the electrode of sensor element 2, and the outer cylinder 24 includes holes 24a and 24b at locations that are not opposite to the hole 21a. Between the inner and outer cylinders 21 and 24, there is a gap wide enough to prevent water from staying therebetween due to surface tension. Water entering the sensor assembly through the holes 24a and 24b in the outer cylinder 24 is immediately discharged out of the holes 24a and 24b through the gap between the outer and inner cylinders 24 and 21. Water, even when entering the outer cylinder 24, is unlikely to impinge directly on the sensor element 2 built in the inner cylinder 21.

3 Claims, 3 Drawing Sheets

OXYGEN SENSOR

BACKGROUND OF THE INVENTION

The present invention relates generally to an oxygen sensor and, more particularly, to an oxygen sensor of the type designed to detect the concentration of oxygen in exhaust gases discharged from internal combustion engines.

One conventional oxygen sensor known to be incorporated in an exhaust pipe of an internal combustion engine includes a protective cover placed around a sensor element to make an exhaust gas flow uniform, as set forth in Japanese Utility Model Laid.Open Publication No. Hei. 1-169350. Another oxygen sensor assembly having a double-structure type protective cover is known from U.S. Pat. Nos. 4597850 and 4683049.

However, problems with such conventional oxygen sensors are that in the case of the single protective cover, an amount of water, which is generated when the internal combustion engine is started up, is likely to reach the sensor element location through a gas inlet hole provided in the protective cover, and in the case of the double protective cover, an amount of water is deposited through a gas inlet hole in the outer protective cover onto the surface of the inner protective cover due to surface tension and then remains stagnant between the outer and inner cylinders. As the internal combustion engine is accelerated, the water stagnating between the inner and outer cylinders due to surface tension is so likely to reach the sensor element location through the gas inlet hole in the inner cylinder.protecting cover that the sensor element may crack or break, although not often. Especially where a heating type sensor with a built-in heater is used with an internal combustion engine, the sensor element is considerably heated within 20 to 80 seconds after it has been started up. When water strikes upon the sensor element in this state, it may often crack and, in the worst case, break down.

An object of this invention is to solve such problems by the provision of an oxygen sensor assembly designed to keep the sensor element in good order even when it is exposed to water scattered in an exhaust pipe at the time of engine start-up.

SUMMARY OF THE INVENTION

According to one aspect of this invention, there is provided an oxygen sensor assembly including a bottomed, inner cylindrical member placed around an oxygen sensor element and having a gas inlet hole at a location opposite to an electrode and an outer cylindrical member placed around said inner cylindrical member and having a gas inlet hole in a location that is not opposite to said gas inlet hole, said inner cylindrical member being spaced away from said outer cylindrical member with a gap having a width large enough to prevent water from staying therebetween due to surface tension.

According to another aspect of the invention, there is provided an oxygen sensor assembly as recited in the first aspect of the invention, in which there is a difference of at least 1.5 mm between the outer radius of said inner cylindrical member and the inner radius of said outer cylindrical member.

According to a further aspect of the invention, there is provided an oxygen sensor assembly as recited in the first or second aspect of the invention, in which the narrowest spacing, as measured in the axial direction, between said gas inlet holes in said inner and outer cylindrical members is at least 3.5 mm.

Water entering from the second gas inlet hole in the outer cylinder member is discharged, without delay, from the gap between the outer and inner cylindrical members through the gas inlet in the outer cylindrical member. Water entering the outer cylindrical member is unlikely to strike on the sensor element built in the inner cylindrical member. Thus, there is little possibility that water may impinge upon the oxygen sensor element; that is, there is nothing unusual with the sensor element like its cracking or breaking-down.

BRIEF DESCRIPTION OF THE DRAWINGS

Embodiment of the invention will now be described, by way of example, with reference to the accompanying drawings, in which.

DETAILED DESCRIPTION OF THE INVENTION

Figure 1:
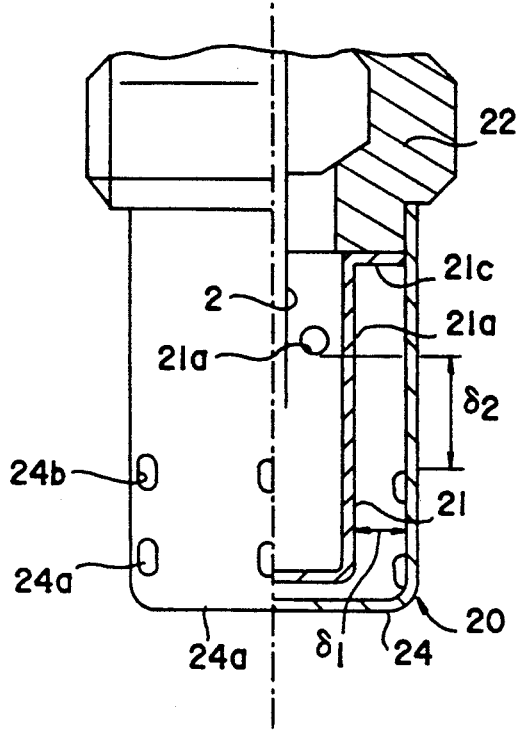
FIG. 1 is a partially cut-away, sectional view illustrating the first embodiment of the invention.

The first embodiment of the invention is illustrated in FIG. 1.

As illustrated, an oxygen sensor assembly 20 comprises a bottomed, inner cylindrical member 21 and a bottomed, outer cylindrical member 24. The inner cylinder 21 is joined to a housing 22 at its flange location 21c and is provided with a plurality of holes 21a around and in a sensor element location in the inner cylinder 21. Around the inner cylinder 21, the bottomed, outer cylinder 24 is joined to the housing 22 and is provided with a plurality of holes 24a and 24b in locations axially spaced away from the holes 21a in the inner cylinder 21. Between the outer surface of the inner cylinder 21 and the inner surface of the outer cylinder 24, there is a gap $\delta_1$ that is wide enough to prevent waterdrops from staying therebetween due to surface tension, say, of the order of at least 1.5 mm, preferably at least 2.0 mm.

Water deposition tests were done with oxygen sensors placed at normal sensor locations in the exhaust pipes of internal combustion engines.

TEST 1

Used to this end were oxygen sensors with varying gaps $\delta_1$ between the outer surfaces of the inner cylinders and the inner surfaces of the outer cylinders. In this test, the narrowest spacing $\delta_2$ measured in the axial direction between the gas inlet holes in the inner and outer cylinders was set to 3.5 mm. The results are plotted in FIG. 2.

Figure 2:
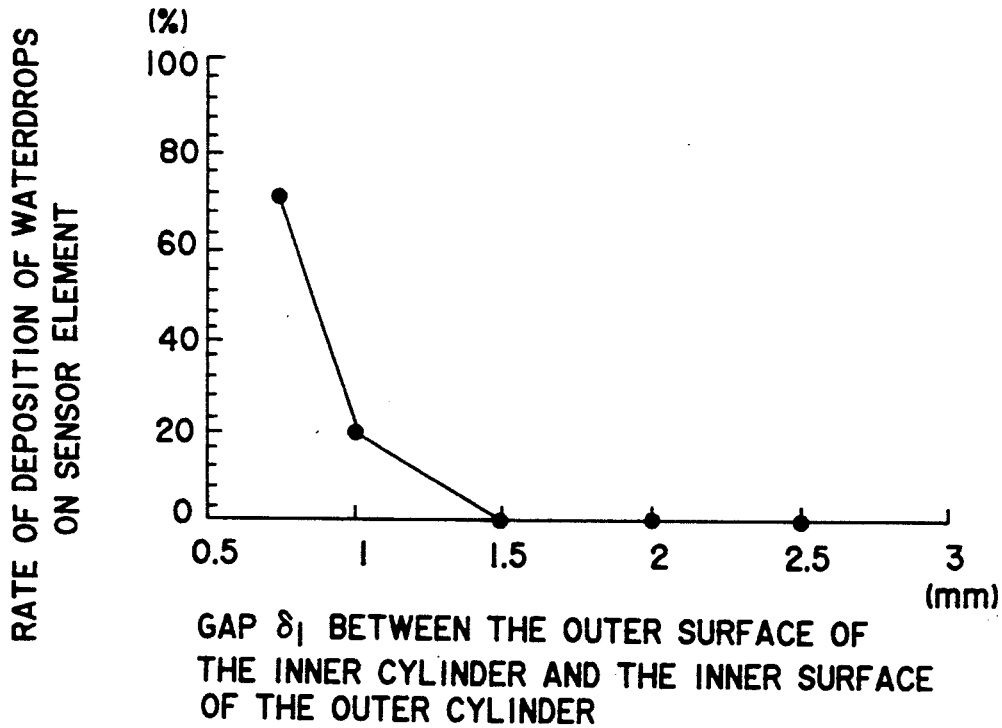
FIG. 2 is an experimental data diagram showing the relationship between the gap between the outer surface of the inner cylinder and the inner surface of the outer cylinder and the rate of deposition of waterdrops.

The experimentation, the results of which are shown in Fig. 2, was done to observe in what state waterdrops were deposited on the sensor elements with varying gap $\delta_1$ between the outer surfaces of the inner cylinders and the inner surfaces of the outer cylinders. In each test run, 10 sensors having the same gap were used. Water was forcedly poured through the exhaust pipe located on the upperstream side of the sensor location at a rate of 50 cc/min. The internal combustion engine was raced three times after it had been idled for 2 minutes. To confirm whether or not water was deposited on the sensor element, the water used was colored. Whether or not water was deposited on the sensor element was visually observed to find the rate of deposition of waterdrops. If waterdrops more than about 0.2 μcc were deposited on the sensor element, then it was taken as being significant. Test 1 was performed with oxygen sensors including protective covers with gaps $\delta_1$ of 0.75, 1.0, 1.5, 2.0 and 2.5 mm between the outer surfaces of the inner cylinders and the inner surfaces of the outer cylinders.

As can be seen from FIG. 2, no water deposition was found when the gap $\delta_1$ was 1.5 mm or more. From the results of Test 1, it was verified that there is little possibility that water may enter the oxygen sensor through the holes 21a in the inner cylinder 21, because the water entering the outer cylinder 24 through the holes 24a and 24b is immediately discharged out of the holes 24a and 24b.

TEST 2

Figure 3:
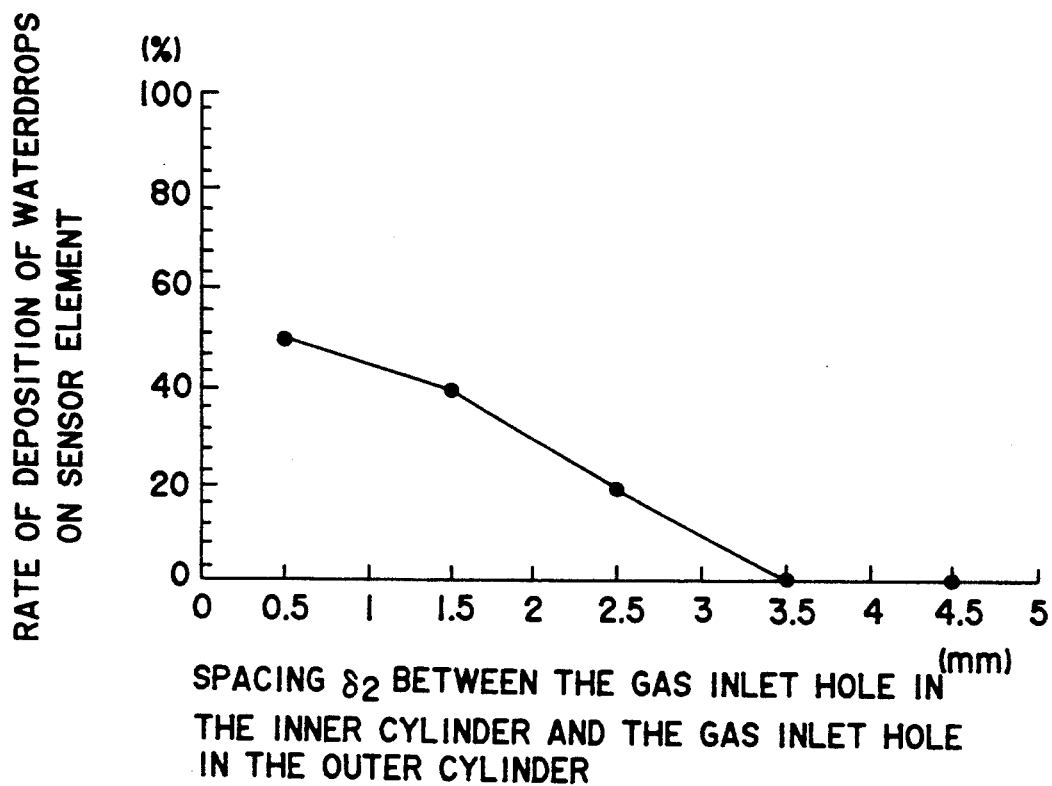
FIG. 3 is an experimental data diagram showing the relationship between the narrowest spacing, as measured in the axial direction, between the gas inlet holes in the inner and outer cylinders and the rate of deposition of waterdrops.

Used to this end were oxygen sensor assemblies varying in the narrowest spacing $\delta_2$, as measured in the axial direction, between the holes in the inner and outer cylinders, all lying at locations opposite to the sensor elements. The results are plotted in FIG. 3. The experimentation, the results of which are shown in FIG. 3, was done to find how water deposition changed with a variation in said narrowest spacing $\delta_2$. In each test run, 10 sensor assemblies, each with the gap $\delta_1$ between the outer surface of the inner cylinder and the inner surface of the outer cylinder fixed at 2.0 mm, were used. Water was forcedly poured through the exhaust pipe located on the upperstream side of the sensor location at a rate of 50 cc/min. The internal combustion engine was raced three times after it had been idled for 2 minutes. To confirm whether or not water was deposited on the sensor element, the water used was colored. Whether or not water was deposited on the sensor element was visually observed to find the rate of deposition of waterdrops. If waterdrops more than about 0.2 μcc were deposited on the sensor element, then it was taken as being significant. Test 2 was carried out with oxygen sensor assemblies having protective covers with the narrowest spacings $\delta_2$ of 0.5, 1.5, 2.5. 3.5 and 4.5 mm.

As can be seen from FIG. 3, no water deposition was found when $\delta_2$ was 3.5 mm or more. It is desired that the spacing $\delta_2$ be at least 3.5 mm, more particularly at least 4.5 mm.

Figure 4:
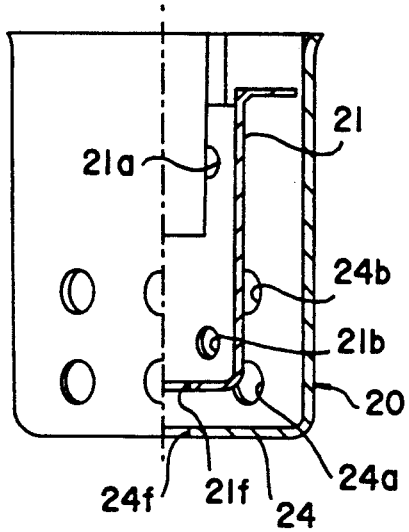
FIG. 4 is a partially cut.away, sectional view of the second embodiment of the invention.

Referring to FIG. 4, there is shown the second embodiment of the invention, wherein an inner cylindrical member 21 is provided with a first hole 21a at a location opposite to a sensor element and additionally includes a second hole 21b at a location not opposite to the sensor element. More specifically, the second hole 21b is positioned at a location axially spaced away from the first hole 21a and circumferentially eccentric with respect to holes 24a and 24b in an outer cylindrical member 24. This arrangement is to prevent waterdrops from entering the inner cylinder 21 directly from the hole 21b through the holes 24a and 24b and to guide waterdrops entering through the holes 24a and 24b to the second hole 21b, thereby reducing the amount of waterdrops flowing toward the hole 21a. In the second embodiment, it is noted that the inner and outer cylinders have holes 21f and 24f respectively in their ends. It is also noted that other parts are substantially similar to those described in connection with the first embodiment; that is, they are shown by the same reference numerals and so are not explained.

Figure 5:
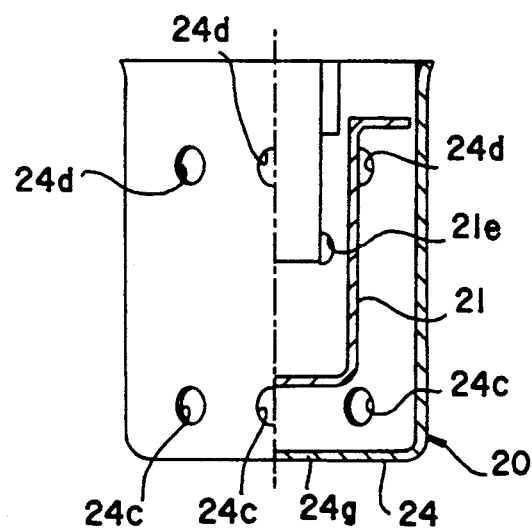
FIG. 5 is a partially cut.away, sectional view of the third embodiment of the invention.

The third embodiment of the invention is illustrated in FIG. 5.

An outer cylindrical member 24 is provided with holes 24c and 24d axially spaced away from each other. At a location halfway between the holes 24c and 24d and opposite to the axis there is provided a hole 21e. Even with this arrangement, it is possible to prevent water from penetrating directly into the inner cylinder 21 through the holes 24c and 24d in the outer cylinder 24 and the hole 21e in the inner cylinder 21. It is noted that the outer cylinder has a hole 24g in its end.

It is understood that the inner and outer cylinders may be fixed to the housing by means other than that illustrated. It is also understood that the shape and structure of the protective cover of the oxygen sensor assembly according to this invention are not limited to those illustrated and described. Thus, various modification or changes may be made the invention without deviating from the spirit and scope as defined in the appended claims, as will be apparent to one of ordinary skill in the art.

According to this invention described above, there is provided an oxygen sensor assembly which enables water entering through the gas inlet holes in the outer cylindrical member to be discharged out easily without delay, making it unlikely to cause water to reach the sensor element location built in the inner cylindrical member through the gas inlet holes therein. Thus, it is possible to prevent the oxygen sensor from cracking, breaking down or otherwise failing.

We claim:

1. An oxygen sensor assembly comprising in combination:
   a bottomed, inner cylindrical member placed around an oxygen sensor element and including a gas inlet hole at a location opposite to an electrode,
   an outer cylindrical member placed around said inner cylindrical member and including a gas inlet hole at a location axially spaced away from said gas inlet hole in said inner cylindrical member and opposed away from said sensor element, and
   a gap provided between said inner and outer cylindrical members, said gap being wide enough to prevent water from staying therebetween due to surface tension.

2. An oxygen sensor assembly as claimed in claim 1, wherein there is a difference of at least 1.5 mm between the outer radius of said inner cylindrical member and the inner radius of said outer cylindrical member.

3. An oxygen sensor assembly as claimed in claim 1 or 2, wherein the narrowest spacing, as measured in the axial direction, between said gas inlet holes in said inner and outer cylindrical members is at least 3.5 mm.

* * * * *